United States Patent [19]

Cotty et al.

[11] 4,049,803
[45] Sept. 20, 1977

[54] AUGMENTATION OF BLOOD LEVELS OF ASPIRIN

[75] Inventors: Val F. Cotty, Westfield; Francis J. Sterbenz, Somerset; Kenneth J. Melman, Mountainside, all of N.J.

[73] Assignee: Bristol-Myers Company, New York, N.Y.

[21] Appl. No.: 680,307

[22] Filed: Apr. 26, 1976

[51] Int. Cl.² .......................................... A61K 31/615
[52] U.S. Cl. ................................................... 424/233
[58] Field of Search .............................. 424/230, 233

[56] References Cited
PUBLICATIONS

Brennan et al., *British Journal of Clinical Practice*, vol. 24, No. 7 July 1970, pp. 293–295.
*Handbook of Non-Prescription Drugs*, 1969 Ed.
Table III, "Examples of o-t-c Internal Analgesics", *Facts and Comparisons*, June 1957, p. 155.

*Primary Examiner*—Stanley J. Friedman
*Attorney, Agent, or Firm*—Holtzman, Irving; Mentis, George A.; Mugford, David J.

[57] ABSTRACT

The normal dosage of 10 grains (648 mg.) of aspirin, when combined with about 5 to 15, preferably about 10, grains of acetaminophen, yields increased blood levels of unhydrolyzed aspirin shortly and for extended periods after oral ingestion; a small addition of caffeine enables attainment of still higher blood levels of aspirin.

13 Claims, No Drawings

AUGMENTATION OF BLOOD LEVELS OF ASPIRIN

This invention relates to compositions and methods designed to augment the blood levels of aspirin or acetylsalicylic acid (hereinafter sometimes referred to as ASA) in animals, and particularly in humans, after the administration of compositions containing ASA. More particularly, it concerns the augmentation of ASA blood levels in humans after oral administration of compositions containing ASA.

ASA has been observed to produce pharmacological responses which are not produced by sodium salicylate. Adams and Cobb (1963) observed a persistent delay in the appearance of the erythema produced by thurfyl nicotinate following the ingestion of 10 grains of ASA but not sodium salicylate. Lin et al (1967) blocked the pain produced by bradykinnin with sodium ASA but obtained no effect with sodium salicylate. ASA, but not sodium salicylate, blocks the second wave of thrombocyte aggregation (O'Brien 1968).

There is also considerable evidence that ASA is therapeutically more potent than salicylic acid. Lester et al (1946), Margolin (1960) and Lasagna (1961) state that ASA was a more effective analgesic than salicylic acid in their clinical trials. Houde et al, (1965) observed that "in equimolar doses, aspirin produced significantly more pain relief than sodium salicylate - despite the well-known fact that aspirin is rapidly hydrolyzed to salicylic acid and the total salicylate level achieved in the blood is as high or higher after the ingestion of sodium salicylate than after aspirin". Although a different mechanism may be involved, Bywaters (1963) and Duthie (1963) have expessed the view that aspirin is superior to salicylic acid as an anti-inflammatory agent. Seed (1965) has shown that acetylsalicylic acid is a more potent antipyretic than salicylic acid when administered in equimolar doses.

From the above, it should be apparent that since ASA achieves its therapeutic effects via transmission through the bloodstream, and hydrolyzation (i.e. to salicylic acid) is detrimental to such achievement, it would be highly advantageous if some means could be discovered for maximizing the concentration of unhydrolyzed ASA in the blood following oral administration thereof.

It is accordingly an object of this invention to provide means for relatively increasing or maximizing the level or concentration of ASA in the blood shortly or over extended periods following oral administration thereof.

Another object of this invention is the provision of a composition containing ASA which when orally administered results in an increased level or concentration of ASA in the blood.

Still another object of this invention is the provision of such a composition which can be expected to yield increased or additional therapeutic effects relative to those obtained with ASA alone.

A further object of this invention is the provision of a method for increasing, augmenting or maximizing the level or concentration of ASA in the blood following oral administration thereof.

Other objects and advantages will appear as the description proceeds.

The attainment of one or more of the above objects is made possible by our invention which includes the oral administration of a dose of a mixture containing about 5 to 15 grains, preferably about 10 grains, of acetaminophen and about 10 grains of acetylsalicylic acid adapted for substantially concurrent release in the body.

The effect that APAP has in augmenting the blood level of unhydrolyzed ASA in animals when the two are administered together is referred to herein as the "aspirin sparing" effect. The mechanism of this effect is not clearly understood. In in vitro experiments in which the hydrolysis of ASA was measured, no retardation of the deacetylation of ASA was observed when APAP was added with the ASA to rat liver homogenates or to human whole heparinized blood. Neither was inhibition of the in vitro hydrolysis of ASA observed in the blood of human subjects following ingestion of APAP-aspirin tablets. The observed augmentation of ASA blood levels in human subjects i.e. the aspirin sparing effect of APAP, therefore, does not appear to be due to enzyme inhibition.

Aspirin is known to be hydrolyzed to a considerable extent in the "first pass" through the liver following absorption into the portal circulation. Moreover, a number of compounds have the ability to modify hepatic blood flow and consequently, hepatic extraction of drugs. It may be that the larger amount of aspirin in blood following the ingestion of APAP-ASA mixtures of this invention, as compared to aspirin alone, is due to a reduction in the hepatic extraction of aspirin. However, the literature contains no direct evidence for the sparing of aspirin by this mechanism.

In an article by Brennan and Sripathy entitled "A Safe Aspirin Preparation", Brit. Jour. Clinical Practice, 24 No. 7 (July 1970) 293–5, an aspirin tablet is described which is formulated and constructed to avoid the reported inducement of gastric irritation and hemorrhage by aspirin. This tablet contains "5 gr. (300 mg.) of aspirin in a central enteric-coated core which resists digestion by gastric juice, and liberates the aspirin only into the small intestine." The article states that "Absorption is, however, delayed by about 1 hour by this procedure, and to overcome this the enteric core is surrounded by a layer containing 4 gr. (200 mg.) of paracetamol. The latter is rapidly released in the stomach and provides analgesia of rapid onset". Thus, this article obviously fails to recognize the basic concept of the present invention and its improved and unexpected results in raising the blood level of ASA, and in fact describes a tablet structure which even inherently could not be expected to yield such results because of the rapid absorption of the paracetamol about an hour before initiation of aspirin absorption.

Further, although several types of aspirin tablets have been and are being marketed which are described as containing acetaminophen, none are known which contain more than about 3.5 grains of aspirin, corresponding to a two tablet dose of about 7 grains of aspirin. The acetaminophen and other drugs present in these tablets are apparently included not merely for their individual pharmaceutical effects, but to also effectuate the definitive purpose of reducing the resulting dose of aspirin significantly below the normal 10 grain dosage, whereby the resulting blood level of aspirin would be expected, and in fact intended, to be correspondingly reduced.

As stated above, the dosage quantity of the mixture of this invention may contain about 5 to 15 grains, preferably about 7 to 12 grains, and optimally about 10 grains (i.e. about equal to the ASA) of the APAP. Such mixture will generally contain the normal 10 grain dosage of ASA, but this amount may be increased to about 12 or even 15 grains of ASA, with corresponding increase in proportions of the APAP, when for some reason even higher ASA blood levels are desired.

The term dose is used herein in the sense that it is usually employed in the pharmaceutical arts. A dose of the APAP-ASA mixture would therefore be the total quantity of the mixture to be taken at any one particular time. This may be in the form of a powder, a solution or slurry, or in the form of one or more tablets. Moreover, when incorporated in a tablet, the tablet may take the form of a homogeneous tablet or a multilayered tablet or the conventional or the sustained release type, provided that both the ASA and APAP are released substantially concurrently in the body, i.e. within the period of no more than about 30 minutes, preferably no more than about 10 minutes, optimally simultaneously. The mixture may accordingly be released relatively promptly entirely in the stomach, entirely in the intestines as by means of an enteric coating, or over an extended period of time in either or both the stomach and intestines.

As a further feature of this invention, it has been found generally advantageous to also incorporate in the compositions of this invention a small quantity of caffeine, whereby to attain an even further beneficial "aspirin sparing" effect. When caffeine is employed, the quantity may be varied somewhat, being then ordinarily employed in the range of about 0.5 to 4, preferably about 0.5 to 2 grains per dose of the APAP-ASA composition.

In preparing in known manner tablets containing the present mixtures, there may be incorporated prior to or during tabletting the conventional tabletting aids or ingredients. Typical among these materials there may be mentioned: binders, disintegrants, lubricants, diluents, colors, surfactants or wetting agents, etc. These are more specifically exemplified by the following:
  binders: microcrystalline cellulose, lactose, sucrose;
  disintegrants: corn starch, potato starch, sodium starch glycolate;
  lubricants: magnesium stearate, talc, stearic acid;
  diluents: lactose, sucrose;
  surfactants: sodium lauryl sulfate.

It may sometimes be advantageous to also incorporate in these tablets other pharmaceutically active ingredients. By way of illustrating these other pharmaceutically active materials, the following may be mentioned: other analgesics such as propoxyphene; decongestants such as phenylpropanolamine (or the hydrochloride), phenylephrine (or the hydrochloride); antihistamines such as methapyrilene (or its hydochloride), diphenhydramine (BENADRYL), chlorpheniramine; antacids such as calcium carbonate, magnesium hydroxide, aluminum hydroxide. However, in the preferred embodiments of this invention, the pharmaceutically active material will consist essentially of the APAP-ASA dosage mixture.

The increased ASA blood levels attainable with the dosage mixtures of this invention generally appear after about 10 minutes following initiation of absorption, and remain over extended periods of up to about 4 to 6 hours.

The following Examples are only illustrative of this invention and are not to be regarded as limitative. All amounts and proportions referred to herein and in the appended claims are by weight unless otherwise indicated.

EXAMPLE 1

The following test medications were prepared as powders:

10 grains ASA + 5 grains APAP
10 grains ASA + 5 grains APAP + 1 grain caffeine
10 grains ASA + 5 grains APAP + 2 grains caffeine
10 grains ASA + 10 grains APAP
10 grains ASA + 10 grains APAP + 1 grain caffeine
10 grains ASA + 10 grains APAP + 2 grains caffeine
10 grains ASA Each dosage was slurried in 50 ml. of water at 20° C just before administration. It was followed by 50 ml of "rinse" water swallowed from the same beaker. Each of the seven test medications was administered to each of three human subjects according to a statistical randomization on each test day in a contemporaneous, multiple crossover design. During the experiment, each of the 21 subjects received a different medication on each of seven spaced test days. All dosing was done at the same time on each test day. Details of the nature and preparation of the human volunteers were described previously (Cotty et al 1965) "Blood Levels of Aspirin following the Ingestion of Commercial Aspirin Containing Tablets by Humans", J. Pharm. Sci. 54, 868-870.

Blood specimens were drawn before and at 20, 40 and 60 minutes after the administration of the various doses of analgesics. Aspirin and salicylic acid analyses were performed by the semi-automatic procedure of Ederma et al (1966) ("Use of Automated Systems in Drug Investigation" in "Automation of Analytical Chemistry", Mediad Inc., New York p. 228-231) which is highly specific and is unperturbed by the presence of other salicylates or their conjugates. This method is unaffected by the presence of acetaminophen and has been used to monitor the microcontamination of APAP tablets by airborne aspirin.

Table I below presents the average ASA blood concentrations as determined by the above procedure in the human subjects receiving the above series of powdered medicaments, and significance test results by analysis of variance.

TABLE I

ASA Blood Concentrations ($\mu$g/ml)

Those preparations joined by a solid line are not significantly different from each other at an overall 0.05 level (via analysis of variance).

20 Minutes 6.40 (10 gr. ASA + 10 gr. APAP + 1 gr. caffeine)
6.26 (10 gr. ASA + 10 gr. APAP)
5.90 (10 gr. ASA + 10 gr. APAP + 2 gr. caffeine)
5.74 (10 gr. ASA + 5 gr. APAP + 2 grs. caffeine)
5.08 (10 gr. ASA + 5 gr. APAP)
4.86 (10 gr. ASA + 5 gr. APAP + 1 gr. caffeine)
3.94 (10 gr. ASA)

40 Minutes 5.96 (10 gr. ASA + 10 gr. APAP + 2 gr. caffeine)
5.81 (10 gr. ASA + 10 gr. APAP + 1 gr. caffeine)
5.47 (10 gr. ASA + 5 gr. APAP + 2 gr. caffeine)
5.40 (10 gr. ASA + 10 gr. APAP)
5.21 (10 gr. ASA + 5 gr. APAP)
4.40 (10 gr. ASA + 5 gr. APAP + 1 gr. caffeine)
3.82 (10 gr. ASA)

60 Minutes

-continued 4.75 (10 gr. ASA + 10 gr. APAP + 2 gr. caffeine)
    4.33 (10 gr. ASA + 10 gr. APAP)
    4.22 (10 gr. ASA + 10 gr. APAP + 1 gr. caffeine)
    4.00 (10 gr. ASA + 5 gr. APAP + 2 gr. caffeine)
    3.68 (10 gr. ASA + 5 gr. APAP)
    3.56 (10 gr. ASA + 5 gr. APAP + 1 gr. caffeine)
    2.81 (10 gr. ASA)

As shown in the above Table, all 10 grains APAP combinations and the 5 grains APAP + 2 grains caffeine combination produced significantly higher ASA levels than 10 grains ASA alone at all time periods. At 40 and 60 minutes, the 5 grains APAP + 10 grains ASA combination was also significantly higher than 10 grains ASA alone. For a fixed amount of APAP (5 or 10 grains), no significant differences were observed among the three formulations with various amounts of caffeine. However, at 20 and 40 minutes, for formulations with 1 grain caffeine, the 10 grains APAP combination produced a significantly higher level of ASA than the 5 grains APAP combination. No significant interaction between APAP and caffeine was obtained at any time period, and comparisons of the 0, 1, and 2 grains caffeine effects on ASA levels gave no significant differences at any time periods. The combined 10 grain APAP non-caffeine medications, however, gave significantly higher ASA levels than the combined 5 grain APAP non-caffeine medications. Significance of the APAP effect was at the 0.05 level at 20 minutes and at the 0.08 and 0.06 level at 40 and 60 minutes respectively.

EXAMPLE 2

A batch of homogeneous tablets was prepared, each having the following formula:

Formula No. 125

| Per tablet | | Ingredients | Per 2000 tablets |
|---|---|---|---|
| 324 mg. | 1. | N-Acetyl-p-aminophenol | 648.0 Gm. |
| | 2. | Cellulose, Microcrystalline | 100.0 |
| | 3. | Corn starch | 100.0 |
| | 4. | Corn starch | 50.0 |
| | 5. | Deionized water | 450.0 |
| 324 mg. ASA | 6. | Aspirin, 10% Starch | 720.0 |
| | 7. | Hydrogenated Castor Oil | 10.0 |
| | | | 1628.0 Gm. |

The following procedure is used to prepare the tablets:
a. Blend 1, 2 and 3 in a 10 quart Hobart pot.
b. Prepare a paste of 4 in 5 by steam in a 5 quart steam jacketed Hobart pot.
c. Granulate A with B and pass through a No. 8 mesh screen.
d. Dry in the Glatt Fluid Bed Dryer (40° C).
e. Pass through a No. 14 mesh screen.
f. Add 6 (previously passed through No. 14 mesh screen) and 7, and blend in Twin Shell Blender.
g. Compress on the Stokes Rotary Multi-Layer Tablet Press.

EXAMPLE 3

A series of blood panels, designed as a two-way crossover were carried out in which 20 human subjects each received two tablets of commercial aspirin (10 grains aspirin) and on other days two tablets of Formulation No. 125 (10 grains aspirin plus 10 grains APAP). Blood samples, drawn at 0, 10, 20, 40, and 60 minutes were analyzed for aspirin (ASA) and total salicylate (TSA). Pre-dose, zero-time readings were subtracted and all values are expressed in $\mu g/ml$ blood.

Statistical analyses indicated that no significant difference exists between the two preparations in TSA values at any of the time periods studied. Regarding ASA, Formulation No. 125 was significantly higher at the 0.05 level at 20, 40 and 60 minutes only.

The average ASA and total salicylate blood levels obtained with the commercial ASA tablets and combination tablets of ASA and APAP are given in Table II below. TSA blood levels were not significantly different for any time interval. ASA levels, on the other hand, were significantly higher for the APAP-ASA combination at 20, 40 and 60 minutes after drug administration.

TABLE II

| | Average Blood Concentrations ($\mu g/ml$) | | | | | |
|---|---|---|---|---|---|---|
| | TSA | | | ASA | | |
| Minutes | ASA | ASA+APAP | p | ASA | ASA+APAP | p |
| | | (No. 125) | | | (No. 125) | |
| 10 | 4.97 | 4.84 | .96 | 3.71 | 4.09 | .77 |
| 20 | 13.73 | 17.50 | .37 | 5.20 | 9.57 | .02 |
| 40 | 26.01 | 30.10 | .39 | 4.86 | 9.59 | .005 |
| 60 | 32.81 | 36.31 | .34 | 3.32 | 9.63 | .0002 |

These studies indicate that APAP, when co-administered with aspirin, results in ASA levels which are significantly higher than those obtained with the same dose of ASA alone. This effect cannot be attributed to "dosage form" since administration of the medicaments as slurried powders avoided differences in the properties of dosage form (e.g. differences in disintegration time and dissolution rate) and eliminate manufacturing variables associated with tablets. In the study with tablets, TSA levels were not significantly different throughout. Hence, aspirin absorption was not affected.

EXAMPLE 4

A series of capsules were prepared to study ASA blood levels in humans after the administration of various compositions. The study included compositions not forming part of this invention for purposes of comparison. Table III below gives the data concerning the content of each capsule and the number of capsules administered at any one time, i.e. the dose.

TABLE III

| Ex. No. | Amt. of Drug per Capsule in Grains | | | No. of Capsules |
|---|---|---|---|---|
| | ASA | APAP | Caffeine | |
| 4-1 | 5 | — | — | 1 |
| 4-2 | 5 | 2½ | .625 | 2 |
| 4-3 | 5 | 5 | — | 2 |
| 4-4 | 5 | — | 1 | 2 |
| 4-5 | 3⅓ | 6⅔ | — | 3 |
| 4-6 | 5 | 2½ | — | 2 |
| 4-7 | 5 | — | 2 | 2 |
| 4-8 | 5 | — | .5 | 2 |

Examples 4-2, 4-3 and 4-6 are illustrative of the present invention.

A series of bioequivalence studies were conducted in which twelve human subjects, divided into four groups of three each, orally received each of the dosages described in Table III above. Blood samples drawn at 0, 30, 60, 90 minutes, 2 hours and 4 hours were analyzed for aspirin (ASA) and total salicylate (TSA). All pre-dose, zero-time readings were subtracted, and all values are expressed in $\mu g$ per ml of whole blood.

The results indicated that APAP, when administered with aspirin, increased blood levels of unhydrolyzed ASA. Five grains of APAP administered with 10 grains of ASA produced higher blood levels of ASA than 10 grains of aspirin alone, and the addition of 10 grains of APAP resulted in still higher levels of ASA in the blood of the subjects. Increasing the APAP dosage to 20 grains with 10 grains of ASA appeared to produce no greater ASA blood concentrations. Caffeine also increased ASA blood levels but with no apparent dose response. One, two or four grains in combination with 10 grains ASA resulted in about the same blood levels of ASA.

The invention has been disclosed with respect to preferred embodiments, and it is to be understood that modifications and variations thereof obvious to those skilled in the art are to be included within the spirit and purview of this application and the scope of the appended claims.

What is claimed is:

1. As a composition of matter, a dose of a mixture containing about 10 grains of acetaminophen and about 10 grains of acetylsalicylic acid, said dose being in the form of a powder, solution, slurry or one or more tablets and being adapted for substantially concurrent release of both of said acetaminophen and said acetylsalicylic acid to the body.

2. A composition according to claim 1 in which said dose takes the form of two tablets each containing about 5 grains of acetaminophen and about 5 grains of acetylsalicylic acid.

3. A composition according to claim 1 in which said dose takes the form of two capsules each containing about 5 grains of acetaminophen and about 5 grains of acetylsalicylic acid.

4. A composition according to claim 1 also containing from about 0.5 grains to 2 grains of caffeine.

5. As a composition of matter, a dose of a mixture containing about 5 grains of acetaminophen and about 10 grains of acetylsalicylic acid, said dose being in the form of a powder, solution, slurry or one or more tablets and being adapted for substantially concurrent release of both of said acetaminophen and said acetylsalicylic acid to the body.

6. A composition according to claim 5 in which said dose takes the form of two capsules each containing about 2½ grains of acetaminophen and 5 grains of acetylsalicylic acid.

7. A compressed tablet comprising a homogeneous mixture of about 5 grains of acetaminophen and 5 grains of acetylsalicylic acid, said tablet being adapted for substantially concurrent release of said acetaminophen and said acetylsalicylic acid to the body.

8. A method for augmenting the blood levels of acetylsalicylic acid in animals which comprises orally administering to said animals a dosage quantity of the composition of claim 1.

9. A method for augmenting the blood levels of acetylsalicylic acid in animals which comprises orally administering to said animals a dosage quantity of the composition of claim 2.

10. A method for augmenting the blood levels of acetylsalicylic acid in animals which comprises orally administering to said animals a dosage quantity of the composition of claim 3.

11. A method for augmenting the blood levels of acetylsalicylic acid in animals which comprises orally administering to said animals a dosage quantity of the composition of claim 4.

12. A method for augmenting the blood levels of acetylsalicylic acid in animals which comprises orally administering to said animals a dosage quantity of the composition of claim 5.

13. A method for augmenting the blood levels of acetylsalicylic acid in animals which comprises orally administering to said animals a dosage quantity of the composition of claim 6.

* * * * *